United States Patent [19]

van Amerongen et al.

[11] Patent Number: 6,117,475
[45] Date of Patent: Sep. 12, 2000

[54] FAT BASED FOOD PRODUCTS COMPRISING STEROLS

[75] Inventors: Marnix P. van Amerongen, Vlaardingen, Netherlands; Lourus Cornelis Lievense, Valinhos, Brazil

[73] Assignee: Lipton, division of Conopco, Inc., Englewood Cliffs, N.J.

[21] Appl. No.: 09/135,719

[22] Filed: Aug. 18, 1998

[30] Foreign Application Priority Data

Aug. 22, 1997 [EP] European Pat. Off. .............. 97202595

[51] Int. Cl.⁷ ..................................................... A23D 9/007
[52] U.S. Cl. ........................... 426/601; 426/611; 552/544
[58] Field of Search ..................................... 426/601, 611

[56] References Cited

U.S. PATENT DOCUMENTS

| | | | |
|---|---|---|---|
| 3,751,569 | 8/1973 | Erickson . | |
| 5,244,887 | 9/1993 | Straub | 514/182 |
| 5,502,045 | 3/1996 | Miettinen | 514/182 |
| 5,892,068 | 4/1999 | Higgins | 552/554 |
| 5,958,913 | 9/1999 | Miettenen | 514/182 |
| 6,025,348 | 2/2000 | Goto | 514/182 |
| 6,031,118 | 2/2000 | van Amerongen | 552/554 |

FOREIGN PATENT DOCUMENTS

| | | |
|---|---|---|
| 041 303 | 11/1983 | European Pat. Off. . |
| 209 176 | 1/1987 | European Pat. Off. . |
| 249 282 | 12/1987 | European Pat. Off. . |
| 470 658 | 2/1992 | European Pat. Off. . |
| WO 92/19640 | 11/1999 | Finland . |
| 143115 | 9/1974 | Netherlands . |
| 149687 | 6/1976 | Netherlands . |
| 155177 | 5/1977 | Netherlands . |
| 155436 | 6/1978 | Netherlands . |
| 178559 | 4/1986 | Netherlands . |
| 1 405 346 | 9/1975 | United Kingdom . |
| 93/38047 | 5/1996 | WIPO . |
| 97/42830 | 5/1997 | WIPO . |
| 98/19556 | 11/1997 | WIPO . |
| 98/01126 | 1/1998 | WIPO . |
| 98/06405 | 2/1998 | WIPO . |
| 98/28990 | 7/1998 | WIPO . |

OTHER PUBLICATIONS

Swern 1979 Bailey's Industrial Gel and Fat Products vol. 1 4$^{th}$ edition John Wiley & Sons, New York p 413–419.
European Search Report dated Dec. 10, 1998.

*Primary Examiner*—Carolyn Paden
*Attorney, Agent, or Firm*—Gerard J. McGowan, Jr.

[57] ABSTRACT

The invention concerns a fat based food product comprising natural fat components which have a blood cholesterol lowering effect in amounts sufficient to obtain a blood cholesterol lowering effect, wherein the fat comprises at least 1% of a sterol composition which comprises sterols of which at least 40% is esterified with fatty acid esters.

11 Claims, No Drawings

FAT BASED FOOD PRODUCTS COMPRISING STEROLS

BACKGROUND OF THE INVENTION

The present invention concerns a fat based food product comprising sterols which have a blood cholesterol lowering effect when the food product is used according to the common needs of the consumer.

In International Application no. WO 92/19640 (Raision Marganiini oy) a substance of beta-sitostanol fatty acid ester is described that can be used as such or added to food. Also a comparison with the use of beta-sitostanol is described.

U.S. Pat. No. 3,751,569 suggests the use of esters of monocarboxylic acid and plant sterols in dietary oils for reducing the cholesterol level.

WO 96/38047 (Unilever) describes the addition of specific levels of phytosterols to fat based food products, the phytosterols being defined as to include phytosterols fatty acid esters.

It has been observed that the stability of fat based food products diminishes by the addition of sterols and stanols thereto, in particular when the sterols/stanols are used at higher levels. As sterols and stanols are not very soluble in fat large crystals thereof are found in the products prepared with these sterols or stanols. For example, very serious crystal formation is observed at 3–4% sterol levels On the other hand, however, the use of these higher levels is often required to obtain the significant cholesterol reduction level that is desired.

It is well known that by esterification with fatty acids, the solubility of sterols/stanols can be increased. However, a disadvantage of this esterification is that it decreases the efficacy of the sterol/stanol compounds to lower the blood cholesterol level. Another disadvantage found in the use of sterol/stanol fatty acid esters is that the absorption of lipophilic micronutrients (like beta-carotene) is decreased (Gyling H K et al (1996) Circulation 6: I-578).

Another disadvantage of using fatty acid-esterified sterol/stanols is found in the production thereof, requiring long processing times and/or high processing costs.

SUMMARY OF THE INVENTION

The disadvantages indicated above were found to be reduced with the present invention, which concerns fat based food products with an optimal ratio of free and esterified sterols. The products of the invention comprise at least 1% of total sterol and sterol fatty acid esters (calculated as free sterols) whereby the degree of esterification of the sterols is in the range of 40%–90%. Preferably, the degree of esterification is in the range of 50–85%, more preferred in the range of 55–80%, and most preferred in the range of 60–70%. It has been observed that such products do not show instability and/or crystal formation, whereas a maximum blood cholesterol lowering efficacy of the sterols is obtained and negative effects on absorption of lipophilic micro-nutrients are avoided. This beneficial effect is in particular suitable for products comprising at least 3% total sterols (present as free and esterified sterols), with a degree of esterification of the sterols in the range of 50–85%. Accordingly, a significant cost reduction can be achieved, as the amount of the relatively expensive sterols can be reduced without a decrease of comparable blood cholesterol lowering efficacy, whereas a further reduction of costs is obtained in the time and processing reduction of the esterification process of the sterols. Hence, advantages are found in optimization of effect, quality (solubility) and production costs.

The invention was found to be in particular beneficial at total sterol levels above 3 wt. % sterol equivalents (total of free sterols and sterol present as ester mixture), and more preferably at levels of at least 5 wt. %. Normally, a sterol level range of 7–15 wt. % provides sufficient to good results when applied in daily consumed food products. The fat based food products, comprising the sterols according to the invention do not form organogels, so that organogels are outside our inventive concept.

DETAILED DESCRIPTION OF THE INVENTION

Where in this application sterols are mentioned, phytosterols, phytostanols, or mixtures thereof are meant. Hence, the term sterols in this application refers to 4-desmethylsterols, 4-monomethylsterols and 4,4'-dimethylsterols, their stanol equivalents, and mixtures thereof in any combination possible. Where in this application, reference is made to sterol esters, fatty acid esters of such sterols/stanols are meant.

The most advantageous level of sterols to be esterified within the teaching of the present invention depends on the fat level in the food product and the total level of sterols therein. At a given total sterol amount in the product, the most advantageous degree of esterification will be lower for high fat levels than for low fat levels (based on total food product). For example, at total sterol equivalent levels of about 10% and at fat levels in the range of 50–90%, the degree of esterification is suitably optimized in the range of 40–75%, whereas at a total sterol equivalent level of about 10% and a fat level in the range of 0–50%, the degree of esterification optimum will be found in the range of 60–90%. Also, higher sterol equivalent levels at a given fat level will lead to optimization at higher degrees of esterification.

Fat based food products are food products (partially) based on fat and regarded by the consumer, as 'fatty type of products'. Examples are yellow fat spreads (containing vegetable fat and/or animal fat such as butterfat), dressings, coffee-creamer, shortenings, cooking and frying oils, fillings and toppings, ice-cream and the like. These products in most cases comprise a particular amount of fat. In some cases, however, products are still regarded as 'fatty type of products', despite a replacement of part or even all the fat by fat replacers. Fat based food products in which the fat is partially or completely replaced by fat replacers are also covered by the term fat based food products of this invention.

The food products as such are common products in the western world, and are used by consumers on a daily basis in amounts different for each individual. The invention is in particular very suitable for yellow fat spreads, dressings, cheese, shortenings, cooking and frying oils and ice cream, with a preference for yellow fat spreads, mayonnaise, dressings, shortenings, cooking and frying oils. On the basis of habits of the consumer in the western world, the invention is preferred to concern particular for yellow fat spreads (including margarines, butter and low fat spreads) and dressings. Yellow fat spreads, for this invention, can comprise 0 (zero) to 90% fat (usually 5–80%). Dressings can comprise 0 to 85% fatty (usually 5–80%), shortenings, cooking and frying oil more than 95% fat.

The preparation of the products of the invention can be carried out in any suitable manner commonly known. Suitably, the sterol/sterol ester mixture can be added and dissolved to the fat prior to combining with the aqueous phase of the product to be prepared.

The optimal degree of esterification of the sterols may also vary with the manner of preparation of the food product.

In a preferred embodiment, the food product is a yellow fat spread comprising 0 to 80% fat, the product comprising an optimal ratio of sterol and sterol esters and a total amount of sterol equivalents (present as free and esterified sterols) of at least 2 wt. % and preferably at least 5 wt. %. In its most preferred embodiment, the amount of sterol equivalents is at least 5 wt. %, with optimal results found when the amount of sterol equivalents is in the range of 7–15 wt. %.

The fat that is applied in these fat based food products can be any fat, such as dairy fat and/or vegetable fat. However, if fat is present, for health reasons the use of one or more vegetable fat sources is preferred. In particular, the use of liquid fats is preferred. The fat can be one single fat or a blend. The use of fat compositions comprising a considerable amount of PUFA rich triglycerides in addition to the use of the sterol/sterol ester mixture is in particular considered highly beneficial. For example, oils of sunflower, safflower, rapeseed, linseed, linola and/or soybean can be used in a preferred embodiment. Also the fat compositions mentioned in Netherlands patent documents no. Nl 143115, Nl 178559, Nl 155436, Nl 149687, Nl 155177, European patent documents EP 41303, EP 209176, EP 249282, and EP 470658 are highly suitable.

If a fat blend is used, it is preferred that it comprises at least 30%, and more preferred at least 45% of polyunsaturated fatty acids, based on the total weight amount of the fat in the fat based food product. So, a strong effect on the cholesterol lowering effect is obtained if use is made of an optimal ratio of sterol and sterol-esters as set forth in this application in a food product in which a fat blend comprising at least 30 wt. % of PUFA rich triglycerides is used.

For fat spreads being a commonly and daily used product in western food eating habits, a preference exists for the use of a mixture of sterol and sterol fatty acid esters, in all the preferred embodiments as set forth above.

Where butterfat is used for preparing spreads of the invention, or where the spreads are butter, it is preferred that the amount of sterol equivalents is in the range of 5–15%, preferably 10–15%. As the consumption of butter is considered less beneficial for consumers health, the present invention is in particular suitable for making spreads containing butter or butter-melanges, as the negative effect associated with the butter consumption can be minimized or even reversed.

For obtaining the optimal amount of sterol-esters, preferably the sterols are esterified with one or more $C_{2-22}$ fatty acids. For the purpose of the invention the term $C_{2-22}$ fatty acid refers to any molecule comprising a $C_{2-22}$ main chain and at least one acid group. Although not preferred within the present context the $C_{2-22}$ main chain may be partially substituted or side chains may be present. Preferably, however the $C_{2-22}$ fatty acids are linear molecules comprising one or two acid group(s) as end group (s). Most preferred are linear $C_{8-22}$ fatty acids as occur in natural oils.

Suitable examples of any such fatty acids are acetic acid, propionic acid, butyric acid, caproic acid, caprylic acid, capric acid. Other suitable acids are for example citric acid, lactic acid, oxalic acid and maleic acid. Most preferred are lauric acid, palmitic acid, stearic acid, arachidic acid, behenic acid, oleic acid, cetoleic acid, erucic acid, elaidic acid, linoleic acid and linolenic acid.

When desired a mixture of fatty acids may be used for esterification of the sterols. For example, it is possible to use a naturally occurring fat or oil as a source of the fatty acid and to carry out the esterification via an interesterification reaction.

In a particular embodiment, the fatty acid mixture contains a high amount (>35%, preferably >45%, further preferred >60%) of polyunsaturated fatty acids (PUFA). This does not only provide the advantage of PUFA itself having good blood cholesterol lowering capacity, but also of the sterols esters prepared with such fatty acids being considered as having a higher solubility and blood cholesterol lowering efficacy in the body.

Preferably fatty acid mixtures of sunflower, safflower, rapeseed, linseed, linola and/or soybean are used. These are typical sources of high PUFA and/or low SAFA. Suitable esterification conditions are for example described in WO 92/19640.

Another advantage of the present invention is that by addition of the sterol mixture of free sterols and fatty acid ester sterols, the amount of hardstock required to make a spreadable product out of above mentioned liquid oils can be reduced, thereby optimizing the amount of PUFA rich glycerides in the product.

EXAMPLE I

Human trial, Intake 3.31 g/d sterols, 65% esterified

The study was conducted with 100 volunteers, between 18 and 65 years of age, with stable body weights and body mass indices and normal dietary patterns. Subjects received during 25 days (3.5 weeks) 30 g/d of a margarine for consumption at lunch and dinner. Fasting blood was sampled after 3.5 weeks. A short run-in period of five days in which the volunteers familiarized themselves with the procedures preceded the actual trial.

The trial margarines were fortified with sterols derived from soybean oil distillates. These sterols were esterified with fatty acids from sunflower seed oil with an esterification rate of 65%. The sterol-ester concentrates were used in spread production together with other edible oils and fats in order to achieve a product with similar fatty acid composition as the non-fortified control (PUFA/MUFA/SAFA=48/29/23%). Final sterol equivalent concentration (as free and esterified sterol) was 11.0% on product. Margarines were kept at 5° C. before delivery to the volunteers and were intended to replace an equivalent amount of the spread habitually used by the volunteers.

Venous blood was obtained from seated volunteers that were at least 10 hours in a fasting state. Plasma was prepared by centrifuging blood for 10 minutes at 3000 g. Plasma total cholesterol concentrations were determined directly. HDL- and LDL-cholesterol levels at screening were determined at a later stage in plasma. LDL-cholesterol was calculated. Plasma obtained during the trial was stored at –80 degree C. for cholesterol analyses.

Analyses showed a decrease in total cholesterol concentration of 7.4% (from 5.15 mM in control group to 4.77 mM in sterol group) and a decrease of 11.8% in LDL-cholesterol concentration (from 3.31 mM to 2.92 mM). HDL-cholesterol concentration was not significantly affected by the test margarine. In conclusion, an intake of 3.31 g of sterols per day of which 65% was esterified with fatty acids lead to a decrease in total cholesterol concentration of 7.4% and a decrease in LDL-cholesterol concentration of 11.8%. The HDL/LDL cholesterol ratio was positively affected by an increase of 14.3%.

EXAMPLE II

Human trial, Intake 3.30 g/d sterols, 85% esterified

The study was conducted with 100 volunteers, between 18 and 65 years of age, with stable body weights and body mass indices and normal dietary patterns. Subjects received during 25 days (3.5 weeks) 25 g/d of a margarine for consumption at lunch and dinner. Fasting blood was sampled after 3.5 weeks.

The trial margarines were fortified with sterols derived from soybean oil distillates. These sterols were esterified with fatty acids from sunflower seed oil with an esterification rate of 85%. The sterol-ester concentrates were used in spread production together with other edible oils and fats in order to achieve a product with similar fatty acid composition as the non-fortified control (PUFA/MUFA/SAFA=48/29/23%). Final sterol equivalent concentration (as free and esterified sterol) was 13.2% on product. Margarines were kept at 5° C. before delivery to the volunteers and were intended to replace an equivalent amount of the spread habitually used by the volunteers.

Venous blood was obtained from seated volunteers that were at least 10 hours in a fasting state. Plasma was prepared by centrifuging blood for 10 minutes at 3000 g. Plasma total cholesterol concentrations were determined directly. HDL- and LDL-cholesterol levels at screening were determined at a later stage in plasma. LDL-cholesterol was calculated. Plasma obtained during the trial was stored at −80 degree C. for cholesterol analyses.

Analyses showed a decrease in total cholesterol concentration of 6.3% (from 5.25 mM in control group to 4.92 mM in sterol group) and a decrease of 9.0% in LDL-cholesterol concentration (from 3.10 mM to 2.82 mM). HDL-cholesterol concentration was not significantly affected by the test margarine. In conclusion, an intake of 3.30 g of sterols per day of which 85% was esterified lead to a decrease in total cholesterol concentration of 6.3% and a decrease in LDL-cholesterol concentration of 9.0%. The HDL/LDL cholesterol ratio was positively affected by an increase of 7.9%.

EXAMPLE III

Human trial, Intake 0.85 g/d sterols, 0% esterified

The study was conducted with 78 volunteers, between 18 and 65 years of age, with stable body weights and body mass indices and normal dietary patterns. Subjects received during 25 days (3.5 weeks) 25 g/d of a margarine for consumption at lunch and dinner. Fasting blood was sampled after 3.5 weeks.

The trial margarines were fortified with sterols derived from soybean oil distillates. These sterols were added as free sterols to the margarine. The sterol concentrates were used in spread production together with other edible oils and fats in order to achieve a product with similar fatty acid composition as the non-fortified control (PUFA/MUFA/SAFA=48/29/23%). Final sterol equivalent concentration (as free sterol) was 3.4% on product. Margarines were kept at 5° C. before delivery to the volunteers and were intended to replace an equivalent amount of the spread habitually used by the volunteers.

Venous blood was obtained from seated volunteers that were at least 10 hours in a fasting state. Plasma was prepared by centrifuging blood for 10 minutes at 3000 g. Plasma total cholesterol concentrations were determined directly. HDL- and LDL-cholesterol levels at screening were determined at a later stage in plasma. LDL-cholesterol was calculated. Plasma obtained during the trial was stored at −80 degree C. for cholesterol analyses.

Analyses showed a decrease in total cholesterol concentration of 3.8% (from 5.06 mM in control group to 4.87 mM in sterol group) and a decrease of 6.1% in LDL-cholesterol concentration (from 3.10 mM to 2.91 mM). HDL-cholesterol concentration was not significantly affected by the test margarine. In conclusion, an intake of 0.85 g of unesterified sterols per day lead to a decrease in total cholesterol concentration of 3.8% and a decrease in LDL-cholesterol concentration of 6.1%. The HDL/LDL cholesterol ratio was positively affected by an increase of 8.2%

EXAMPLE IV

Human trial, Intake 0.85 g/d sterols, 85% esterified

The study was conducted with 100 volunteers, between 18 and 65 years of age, with stable body weights and body mass indices and normal dietary patterns. Subjects received during 25 days (3.5 weeks) 25 g/d of a margarine for consumption at lunch and dinner. Fasting blood was sampled after 3.5 weeks.

The trial margarines were fortified with sterols derived from soybean oil distillates. These sterols were esterified with fatty acids from sunflower seed oil with an esterification rate of 85%. The sterol-ester concentrates were used in spread production together with other edible oils and fats in order to achieve a product with similar fatty acid composition as the non-fortified control (PUFA/MUFA/SAFA=48/29/23%). Final sterol equivalent concentration (as free and esterified sterol) was 3.4% on product. Margarines were kept at 5° C. before delivery to the volunteers and were intended to replace an equivalent amount of the spread habitually used by the volunteers.

Venous blood was obtained from seated volunteers that were at least 10 hours in a fasting state. Plasma was prepared by centrifuging blood for 10 minutes at 3000 g. Plasma total cholesterol concentrations were determined directly. HDL- and LDL-cholesterol levels at screening were determined at a later stage in plasma. LDL-cholesterol was calculated. Plasma obtained during the trial was stored at −80 degree C. for cholesterol analyses.

Analyses showed a decrease in total cholesterol concentration of 2.9% (from 5.25 mM in control group to 5.10 mM in sterol group) and a decrease of 2.3% in LDL-cholesterol concentration (from 3.10 mM to 3.03 mM). HDL-cholesterol concentration was not significantly affected by the test margarine. In conclusion, an intake of 0.85 g of sterols per day of which 85% was esterified lead to a decrease in total cholesterol concentration of 2.9% and a decrease in LDL-cholesterol concentration of 2.3%. The HDL/LDL cholesterol ratio was positively affected by an increase of 2.9%.

EXAMPLE V

Preparation of a Spread 70% Fat 39 parts refined sunflower oil (65% PUFA as linoleic acid) was enriched with 5.7 parts of free sterols and 53.5 parts of sterols esterified with sunflower fatty acid (total sterol equivalent concentration 38.3%). Of this sterol and sterol-ester concentrate, 31 parts were mixed with 25 parts of normal refined sunflower oil, 15 parts of refined rapeseed oil and 11 parts of a refined interesterified mixture of 65 parts fully hardened palm oil and 35 parts fully hardened palm kernel oil. To 82 parts of this fatblend, small amounts of soybean lecithin, monoglyceride, flavours and beta-carotene solution were added.

To 16 parts water, small amounts of whey protein powder, flavour, and citric acid were added to obtain a pH of 4.8.

82 parts of the fat phase composition (containing 70% of fat) and 18 parts of the aqueous phase composition were mixed and kept at 60 degrees C. The mixture was then passed through a Votator line with 2 scraped surface heat exchangers (A-units) and 1 stirred crystallizer (C-unit) in AAC-sequence operating at 800, 800 and 100 rpm respectively. The product leaving the C-unit had a temperature of 11 degrees C. It was filled into tubs and stored at 5 degrees C. A good and stable, high PUFA, high fat-continuous spread enriched with 12% sterols (as free and esterified sterols in ratio 5.7/53.5) was obtained.

EXAMPLE VI

Preparation of a Spread 70% Fat 39 parts refined sunflower oil (65% PUFA as linoleic acid) was enriched with 12.3 parts of free sterols and 37.4 parts of sterols esterified with sunflower fatty acid (total sterol equivalent concentration 35%). Of this sterol and sterol-ester concentrate, 31 parts were mixed with 24 parts of normal refined sunflower oil, 15 parts of refined rapeseed oil and 11 parts of a refined interesterified mixture of 65 parts fully hardened palm oil and 35 parts fully hardened palm kernel oil. To 81 parts of this fatblend, small amounts of soybean lecithin, monoglyceride, flavours and beta-carotene solution were added.

To 17 parts water, small amounts of whey protein powder, flavour, and citric acid were added to obtain a pH of 4.8.

81 parts of the fat phase composition (containing 70% of fat) and 19 parts of the aqueous phase composition were mixed and kept at 60 degrees C. The mixture was then passed through a Votator line with 2 scraped surface heat exchangers (A-units) and 1 stirred crystallizer (C-unit) in AAC-sequence operating at 800, 800 and 100 rpm respectively. The product leaving the C-unit had a temperature of 11 degrees C. It was filled into tubs and stored at 5 degrees C. A good and stable, high PUFA, high fat-continuous spread enriched with 11% sterols (as free and esterified sterols in ratio 12.3/37.4) was obtained.

EXAMPLE VII

Preparation of a Spread 40%

39 parts refined sunflower oil (65% PUFA as linoleic acid) was enriched with 5.7 parts of free sterols and 53.5 parts of sterols esterified with sunflower fatty acid (total sterol equivalent concentration 38.3%). Of this sterol and sterol-ester concentrate 31 parts were mixed with 15 parts of normal refined sunflower oil and with 6 parts of a refined interesterified mixture of 50 parts fully hardened palm oil and 50 parts fully hardened palm kernel oil. To this fatblend small amounts of soybean lecithin, monoglyceride and beta-carotene solution were added.

To 44 parts water, gelatin and small amounts of whey protein powder, flavours, preservative and citric acid were added to obtain a pH of 4.7.

52 parts of the fat phase composition (containing 40% of fat) and 48 parts of the aqueous phase composition were mixed and kept at 60 degrees C. The mixture was then passed through a Votator line with 2 scraped surface heat exchangers (A-units) and 2 stirred crystallizers (C-unit), in ACAC-sequence operating at 500, 1000, 600 and 100 rpm respectively. The product leaving the last C-unit had a temperature of 10 degrees C. It was filled into tubs and stored at 5 degrees C. A good and stable, high PUFA, low fat-continuous spread enriched with 12% sterols (as free and esterified sterols in ratio 5.7/53.5) was obtained.

EXAMPLE VIII

Preparation of a Spread 70% Fat 48 parts refined sunflower oil (65% PUFA as linoleic acid) was enriched with 23.0 parts of free sterols and 25.2 parts of sterols esterified with sunflower fatty acid (total sterol equivalent concentration 38.3%). Of this sterol and sterol-ester concentrate, 31 parts were mixed with 25 parts of normal refined sunflower oil, 15 parts of refined rapeseed oil and 11 parts of a refined interesterified mixture of 65 parts fully hardened palm oil and 35 parts fully hardened palm kernel oil. To 82 parts of this fatblend, small amounts of soybean lecithin, monoglyceride, flavours and beta-carotene solution were added.

To 16 parts water, small amounts of whey protein powder, flavour, and citric acid were added to obtain a pH of 4.8.

82 parts of the fat phase composition (containing 70% of fat) and 18 parts of the aqueous phase composition were mixed and kept at 60 degrees C. The mixture was then passed through a Votator line with 2 scraped surface heat exchangers (A-units) and 1 stirred crystallizer (C-unit) in AAC-sequence operating at 800, 800 and 100 rpm respectively. The product leaving the C-unit had a temperature of 11 degrees C. It was filled into tubs and stored at 5 degrees C. A good and stable spread could not be obtained. The product with 12% sterols (as free and esterified sterols in ratio 23.0/25.2) was sandy due to the presence of unacceptable sterol crystals.

EXAMPLE IX

Preparation of a Dressing 33% Fat 49 parts of water is mixed with 11 parts of various flavour components, preservatives, thickeners and emulsifiers. The mixture is thoroughly mixed in a stainless steel stirred vessel. To this aqueous mixture 20 parts of sunflower oil (65% PUFA as linoleic acid) enriched with sterol and sterol esters is added. This concentrate is prepared by mixing 49 parts refined sunflower oil with 12.3 parts of free sterols and 37.4 parts of sterols esterified with sunflower fatty acids (total sterol equivalent concentration 35%). To above oil in water mixture, 20 parts of normal refined sunflower oil is added, thoroughly mixed for an additional 15 minutes, to obtain a pre-emulsion. The pre-emulsion is brought into a colloid mill (Prestomill PM30) and processed at a split-size between level 15 and 20 and a throughput between level 4 and 6. A good and stable water continuous dressing enriched with 7% sterols as free and esterified sterols (in ratio 12.3/37.4) is obtained.

What is claimed is:

1. Fat based food product comprising at least 1 wt. % sterol equivalents, present as free or as esterified sterols, whereby the degree of esterification of the sterols is in the range of 40%–90%.

2. Fat based food product according to claim 1, wherein the degree of esterification of the sterols is in the range of 50%–85%.

3. Fat based food product according to claim 2, wherein the fat comprises a sterol and sterol-esters mixture in which the amount of esterified sterols is between 55 and 80%.

4. Fat based food product according to claim 3, wherein the fat comprises a sterol and sterol-esters mixture in which the amount of esterified sterols is between 60 and 70%.

5. Fat based food product according to claim 1, wherein the total amount of sterol equivalents, present as free or as esterified sterols, is at least 2 wt. %.

6. Fat based food product according to claim 5, wherein the total amount of sterol equivalents, present as free or as esterified sterols, is at least 5 wt. %.

7. Fat based food product according to claim 1, wherein the fat in the food product comprises butterfat, and the amount of sterol equivalents, present as free or as esterified sterols, is in the range of 5–15 wt. %.

8. Fat based food product according to claim 1, wherein the fat used in the product is a fat comprising at least 30 wt. % of PUFA rich triglycerides, calculated on the total weight of the fat present in the product.

9. The product according to claim 8 wherein said fat used in the product is a fat comprising at least 45 wt. % of PUFA rich triglycerides.

10. Food product according to claim 1 selected from the group of yellow fat spreads, mayonnaise, dressings, shortenings, cooking and frying oils and ice-cream.

11. Yellow Fat spread comprising 0 to 80% fat according to claim 1.

* * * * *